(12) United States Patent
Joshi et al.

(10) Patent No.: US 12,285,519 B2
(45) Date of Patent: *Apr. 29, 2025

(54) TRANS-TYMPANIC MEMBRANE DELIVERY PLATFORM AND USES THEREOF

(71) Applicant: The Medical College of Wisconsin, Inc., Milwaukee, WI (US)

(72) Inventors: Amit Joshi, Sun Prairie, WI (US); Joseph Edward Kerschner, Menomonee Falls, WI (US); Wenzhou Hong, Brookfield, WI (US); Gayatri Sharma, Milwaukee, WI (US)

(73) Assignee: The Medical College of Wisconsin, Inc., Milwaukee, WI (US)

(*) Notice: Subject to any disclaimer, the term of this patent is extended or adjusted under 35 U.S.C. 154(b) by 409 days.

This patent is subject to a terminal disclaimer.

(21) Appl. No.: 17/548,173

(22) Filed: Dec. 10, 2021

(65) Prior Publication Data

US 2022/0096372 A1 Mar. 31, 2022

Related U.S. Application Data

(63) Continuation of application No. 16/859,422, filed on Apr. 27, 2020, now Pat. No. 11,197,820.

(Continued)

(51) Int. Cl.
*A61K 9/51* (2006.01)
*A61K 9/00* (2006.01)
(Continued)

(52) U.S. Cl.
CPC ............ *A61K 9/0046* (2013.01); *A61K 9/127* (2013.01); *A61K 9/5161* (2013.01);
(Continued)

(58) Field of Classification Search
CPC ..................................................... A61K 9/127
See application file for complete search history.

(56) References Cited

U.S. PATENT DOCUMENTS

| | | |
|---|---|---|
| 8,303,990 B2 | 11/2012 | Dyer, Jr. |
| 9,486,405 B2 | 11/2016 | Piu |

(Continued)

FOREIGN PATENT DOCUMENTS

| | | |
|---|---|---|
| CN | 101031282 A | 9/2007 |
| CN | 103006567 A | 4/2013 |

(Continued)

OTHER PUBLICATIONS

Janet R. Casey, and Michael E. Pichichero. "Changes in Frequency and Pathogens Causing Acute Otitis Media in 1995-2003." The Pediatric Infectious Disease Journal, vol. 23, No. 9, Sep. 2004, pp. 824-828. (Year: 2004).*

(Continued)

*Primary Examiner* — Isaac Shomer
(74) *Attorney, Agent, or Firm* — Quarles & Brady LLP

(57) ABSTRACT

Provided herein are methods and composition for trans-tympanic membrane delivery of therapeutic agents such as antimicrobial agents, anti-inflammatory agents, and anti-biofilm agents to the middle ear for rapid, localized treatment and prevention of diseases and conditions associated with a middle ear infection. In particular, provided herein are cationic, anionic, and polymer-based nanoparticles that provide a platform for delivery of therapeutic cargo, as well as cationic, anionic, and polymer-based nanoparticles compositions for rapid, localized delivery of therapeutic agents to the middle ear.

8 Claims, 2 Drawing Sheets

Related U.S. Application Data

(60) Provisional application No. 62/840,632, filed on Apr. 30, 2019.

(51) Int. Cl.
    *A61K 9/127*     (2006.01)
    *A61K 31/546*     (2006.01)

(52) U.S. Cl.
    CPC ......... *A61K 31/546* (2013.01); *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 9,907,812 | B2 | 3/2018 | Bapat |
| 11,197,820 | B2* | 12/2021 | Joshi .................... A61K 9/5153 |
| 2005/0020813 | A1 | 1/2005 | Masignani et al. |
| 2005/0043298 | A1 | 2/2005 | Van Duzer |
| 2008/0124385 | A1* | 5/2008 | Campbell ............... A61P 27/16 |
| | | | 514/230.2 |
| 2009/0232731 | A1* | 9/2009 | Funk .................... A61K 31/337 |
| | | | 424/9.6 |
| 2009/0306225 | A1 | 12/2009 | Lichter et al. |
| 2013/0028962 | A1 | 1/2013 | Zhang |
| 2016/0095902 | A1 | 4/2016 | Lichter et al. |
| 2016/0228357 | A1 | 8/2016 | Lichter et al. |
| 2016/0243028 | A1 | 8/2016 | Lichter et al. |
| 2016/0317647 | A1* | 11/2016 | Ciaramella ............ A61K 48/00 |
| 2017/0368080 | A1* | 12/2017 | Gan ..................... A61K 9/0053 |
| 2018/0000950 | A1 | 1/2018 | Savel et al. |
| 2018/0028645 | A1* | 2/2018 | Ciaramella ........ A61K 31/7115 |
| 2018/0228903 | A1 | 8/2018 | Kohane et al. |
| 2019/0307678 | A1 | 10/2019 | Lichter et al. |
| 2020/0230051 | A1 | 7/2020 | Lichter et al. |
| 2020/0397907 | A1 | 12/2020 | Savel et al. |
| 2022/0040095 | A1 | 2/2022 | Lichter et al. |
| 2022/0040096 | A1 | 2/2022 | Lichter et al. |
| 2022/0040309 | A1 | 2/2022 | Kohane et al. |

FOREIGN PATENT DOCUMENTS

| | | |
|---|---|---|
| EP | 3067045 A1 | 11/2014 |
| EP | 3295943 A1 | 3/2018 |
| WO | 2006029074 A1 | 3/2006 |
| WO | 2018/026764 A1 | 2/2018 |
| WO | 2018226975 A1 | 12/2018 |

OTHER PUBLICATIONS

Carlos Rodrigo. "Prevention of Acute Otitis Media." Clinical Microbiology and Infection, vol. 3, Supplement 3, 1997, pp. 3S55-3858. (Year: 1997).*

Pichichero, M.E. et al. Evolving microbiology and molecular epidemiology of acute otitis media in the pneumococcal conjugate vaccine era. Pediatr Infect Dis J 26, S12-16 (2007).

Post, J.C., et al. Molecular analysis of bacterial pathogens in otitis media with effusion. JAMA 273, 1598-1604 (1995).

Ratner, A.J., et al. Synergistic proinflammatory responses induced by polymicrobial colonization of epithelial surfaces. Proc Natl Acad Sci U S A 102, 3429-3434 (2005).

Ritsema, J.A.S., et al. Relationship between polarities of antibiotic and polymer matrix on nanoparticle formulations based on aliphatic polyesters. Int J Pharm 548, 730-739 (2018).

Samuels, T.L., et al. Association of Gel-Forming Mucins and Aquaporin Gene Expression With Hearing Loss, Effusion Viscosity, and Inflammation in Otitis Media With Effusion. JAMA Otolaryngol Head Neck Surg 143, 810-817 (2017).

Samuels, T.L., et al. Association of microRNA 146 with middle ear hyperplasia in pediatric otitis media. Int J Pediatr Otorhinolaryngol 88, 104-108 (2016).

Sethi, S. et al. Bacterial infection in chronic obstructive pulmonary disease in 2000: a state-of-the-art review. Clin Microbiol Rev 14, 336-363 (2001).

Sethi, S., et al. New strains of bacteria and exacerbations of chronic obstructive pulmonary disease. N Engl J Med 347, 465-471 (2002).

Shen, H., et al. Synergistic induction of MUC5AC mucin by nontypeable Haemophilus influenzae and *Streptococcus pneumoniae*. Biochem Biophys Res Commun 365, 795-800 (2008).

Shimoyama, M., et al. The Chinchilla Research Resource Database: resource for an otolaryngology disease model. Database (Oxford) 2016(2016).

Shriberg, L.D., et al. Otitis media, fluctuant hearing loss, and speech-language outcomes: a preliminary structural equation model. J Speech Lang Hear Res 43, 100-120 (2000).

Siddiq, S. et al. The diagnosis and management of acute otitis media: American Academy of Pediatrics Guidelines 2013. Arch Dis Child Educ Pract Ed 100, 193-197 (2015).

Sierra, A., et al. Non-typeable Haemophilus influenzae and *Streptococcus pneumoniae* as primary causes of acute otitis media in Colombian children: a prospective study. BMC Infect Dis 11, 4 (2011).

Sine, J., et al. Photo activation of HPPH encapsulated in "Pocket" liposomes triggers multiple drug release and tumor cell killing in mouse breast cancer xenografts. Int J Nanomedicine 10, 125-145 (2015).

Strieth, S., et al., Neovascular targeting chemotherapy: encapsulation of paclitaxel in cationic liposomes impairs functional tumor microvasculature. Int J Cancer, 2004. 110(1): p. 117-24.

Talbird, S.E., et al. Residual economic burden of *Streptococcus pneumoniae*- and nontypeable Haemophilus influenzae-associated disease following vaccination with PCV-7: a multicountry analysis. Vaccine 28 Suppl 6, G14-22 (2010).

Ubell, M.L., et al. MUC2 expression in human middle ear epithelium of patients with otitis media. Arch Otolaryngol Head Neck Surg 134, 39-44 (2008).

Ubell, M.L., et al. Mucin gene polymorphisms in otitis media patients. Laryngoscope 120, 132-138 (2010).

Wang, H., et al. Enhanced anti-tumor efficacy by co-delivery of doxorubicin and paclitaxel with amphiphilic methoxy PEG-PLGA copolymer nanoparticles. Biomaterials 32, 8281-8290 (2011).

Weimer, K.E., et al. Coinfection with Haemophilus influenzae Promotes Pneumococcal Biofilm Formation during Experimental Otitis Media and Impedes the Progression of Pneumococcal Disease. J Infect Dis 202, 1068-1075 (2010).

Woodfield, G. et al. Evidence behind the WHO guidelines: hospital care for children: what is the most effective antibiotic regime for chronic suppurative otitis media in children? J Trop Pediatr 54, 151-156 (2008).

Xu, Q., et al. Identification of *Streptococcus pneumoniae* and Haemophilus influenzae in culture-negative middle ear fluids from children with acute otitis media by combination of multiplex PCR and multi-locus sequencing typing. Int J Pediatr Otorhinolaryngol (2010).

Yang, R., et al. Treatment of otitis media by transtympanic delivery of antibiotics. Science translational medicine 8, 356ra120-356ra120 (2016).

Yang, R., et al. Treatment of *Streptococcus pneumoniae* otitis media in a chinchilla model by transtympanic delivery of antibiotics. JCI insight 3, 1 (2018).

Yu, S.-H., et al. Nanoparticle-induced tight-junction opening for the transport of an anti-angiogenic sulfated polysaccharide across Caco-2 cell monolayers. Acta biomaterialia 9, 7449-7459 (2013).

International Search Authority. International Search Report and Written Opinion for application PCT/US2020/030084, mailed on Aug. 6, 2020.

Tang, Y.-D., et al. Abstract. "Sustained release of hydrophobic and hydrophilic drugs from a floating dosage form." International journal of pharmaceutics 336.1 (2007): 159-165.

Filippo Valente, Laura Astolfi, Edi Simoni, Serena Danti, Valeria Franceschini, Milvia Chicca, Alessandro Martini. "Nanoparticle drug delivery systems for inner ear therapy: An overview." Journal of Drug Delivery Science and Technology, vol. 39 (2017), pp. 28-35.

(56) References Cited

OTHER PUBLICATIONS

Adelbary, AA, et al. "Fabrication of levofloxacin polyethylene glycol decorated nanoliposomes for enhanced management of acute otitis media: Statistical optimization, transtympanic permeation and in vivo evaluation." International Journal of Pharmaceutics 559 (2019) 201-209, published Jan. 23, 2019.

Muller, R.H., et al., "Nanosuspensions as particulate drug formulations in therapy Rationale for development and what we can expect for the future." Advanced Drug Delivery Reviews, vol. 47 (2001), pp. 3-19.

Midoux, P., et al., "Lipid-based mRNA vaccine delivery systems." Expert Review of Vaccines, vol. 14(2), 2015, pp. 221-234.

Glezen, W. Paul, "Prevention of acute otitis media by prophylaxis and treatment of influenza virus infections." Vaccine 19 (2001), pp. S56-S58.

Kadry, Ashraf A., et al., "Treatment of experimental osteomyelitis by liposmal antibodies." Journal of Antimicrobial Chemotherapy, vol. 54, 2004, pp. 1103-1108.

Rodrigo, Carlos, "Prevention of Acute Otitis Media" Clinical Microbiology and Infection, vol. 3, Supplement 3, 1997, pp. 3S55-3S58.

Rodrigo, Carlos, "Prevention of Acute Otitis Media", https://www.sciencedirect.com/science/article/pii/S1198743X14649557 accessed Sep. 24, 2020, originally published 1997, 11 printed pages.

Zou, J., et al., "Biocompatibility of Liposome Nanocarriers in the Rat Inner Ear After Intratympanic Administration." Nanoscale Research Letters (2017) 12:372, pp. 1-14.

Google Patents. English Translation of CN103006567A. https://google.com/patent/CN103006567A/en?oq+chitosan-plga+nanoparticle accessed Jun. 9, 2020, original published in Chinese on Apr. 3, 2013.

Ngan, L., et al., "Preparation of chitosan nanoparticles by spray drying, and their antibacterial activity." Research of Chemical Intermediates, vol. 40, 2014, pp. 2165-2175.

Erramouspe, J., et al., "Treatment and Prevention of Otitis Media." The Annals of Pharmacotherapy, vol. 34, Dec. 2000, pp. 1452-1468.

Abdeldaim, G.M., et al. Multiplex quantitative PCR for detection of lower respiratory tract infection and meningitis caused by *Streptococcus pneumoniae*, Haemophilus influenzae and Neisseria meningitidis. BMC Microbiol 10, 310 (2010).

Al-Nemrawi, N.K., et al., Low Molecular Weight Chitosan-Coated PLGA Nanoparticles for Pulmonary Delivery of Tobramycin for Cystic Fibrosis. Pharmaceuticals (Basel), 2018. 11(1).

Ayala-Orozco, C., et al. Au nanomatryoshkas as efficient near-infrared photothermal transducers for cancer treatment: benchmarking against nanoshells. ACS Nano 8, 6372-6381 (2014).

Bakaletz, L.O. Bacterial biofilms in otitis media: evidence and relevance. Pediatr Infect Dis J 26, S17-19 (2007).

Bakaletz, L.O. Immunopathogenesis of polymicrobial otitis media. J Leukoc Biol 87, 213-222 (2010).

Bardhan, R., et al. Tracking of multimodal therapeutic nanocomplexes targeting breast cancer in vivo. Nano Lett 10, 4920-4928 (2010).

Berman, S. Otitis media in developing countries. Pediatrics 96, 126-131 (1995).

Bhattacharya, S.D., et al. High Rates of Colonization with Drug Resistant Hemophilus Influenzae Type B and *Streptococcus pneumoniae* in Unvaccinated HIV Infected Children from West Bengal. Indian J Pediatr (2010).

Bhutta, M.F., et al. Understanding the aetiology and resolution of chronic otitis media from animal and human studies. Dis Model Mech 10, 1289-1300 (2017).

Brouwer, C.N., et al. Health-related quality of life in children with otitis media. Int J Pediatr Otorhinolaryngol 69, 1031-1041 (2005).

Brouwer, C.N., et al. The impact of recurrent acute otitis media on the quality of life of children and their caregivers. Clin Otolaryngol 30, 258-265 (2005).

Chi, D.H., et al. Nasopharyngeal reservoir of bacterial otitis media and sinusitis pathogens in adults during wellness and viral respiratory illness. Am J Rhinol 17, 209-214 (2003).

Cripps, A.W. et al. Prospects for a vaccine against otitis media. Expert Rev Vaccines 5, 517-534 (2006).

Faden, H., et al. Nasopharyngeal flora in the first three years of life in normal and otitis-prone children. Ann Otol Rhinol Laryngol 100, 612-615 (1991).

Farokhzad, O.C. et al. Impact of nanotechnology on drug delivery. ACS Nano 3, 16-20 (2009).

Finkelstein, J.A., et al. Antimicrobial use in defined populations of infants and young children. Archives of Pediatrics & Adolescent Medicine 154, 395-400 (2000).

Finkelstein, J.A., et al. Reducing antibiotic use in children: a randomized trial in 12 practices. Pediatrics 108, 1-7 (2001).

Gok, U., et al. Bacteriological and PCR analysis of clinical material aspirated from otitis media with effusions. Int J Pediatr Otorhinolaryngol 60, 49-54 (2001).

Hall-Stoodley, L., et al. Direct detection of bacterial biofilms on the middle-ear mucosa of children with chronic otitis media. JAMA 296, 202-211 (2006).

Harrison, A., et al. Comprehensive Proteomic and Metabolomic Signatures of Nontypeable Haemophilus influenzae-Induced Acute Otitis Media Reveal Bacterial Aerobic Respiration in an Immunosuppressed Environment. Mol Cell Proteomics 15, 1117-1138 (2016).

Harrison, L.M., et al. The nasopharyngeal bacterial flora in infancy: effects of age, gender, season, viral upper respiratory tract infection and sleeping position. FEMS Immunol Med Microbiol 25, 19-28 (1999).

Hendolin, P.H., et al. Use of multiplex PCR for simultaneous detection of four bacterial species in middle ear effusions. J Clin Microbiol 35, 2854-2858 (1997).

Hong, W., et al. Expression of calcium-binding proteins S100A8, S100A9 and S100A12 in otitis media. Int J Pediatr Otorhinolaryngol 101, 30-36 (2017).

Hong, W., et al. Nontypeable Haemophilus influenzae inhibits autolysis and fratricide of *Streptococcus pneumoniae* in vitro. Microbes Infect 16, 203-213 (2014).

Ita, K.B. Chemical Penetration Enhancers for Transdermal Drug Delivery—Success and Challenges. Curr Drug Deliv 12, 645-651 (2015).

Joshi, A., et al. Radiative transport-based frequency-domain fluorescence tomography. Phys Med Biol 53, 2069-2088 (2008).

Kalcioglu, M.T., et al. Bacteriology of chronic maxillary sinusitis and normal maxillary sinuses: using culture and multiplex polymerase chain reaction. Am J Rhinol 17, 143-147 (2003).

Kaur, R., et al. Simultaneous Assay for Four Bacterial Species Including Alloiococcus otitidis Using Multiplex-PCR in Children With Culture Negative Acute Otitis Media. Pediatr Infect Dis J (2010).

Kerschner, J.E. Bench and bedside advances in otitis media. Curr Opin Otolaryngol Head Neck Surg 16, 543-547 (2008).

Kerschner, J.E., et al. A novel model of spontaneous otitis media with effusion (OME) in the Oxgr1 knock-out mouse. Int J Pediatr Otorhinolaryngol 77, 79-84 (2013).

Kerschner, J.E., et al. Dexamethasone modulation of MUC5AC and MUC2 gene expression in a generalized model of middle ear inflammation. Laryngoscope 126, E248-254 (2016).

Kerschner, J.E., et al. Differential response of gel-forming mucins to pathogenic middle ear bacteria. Int J Pediatr Otorhinolaryngol 78, 1368-1373 (2014).

Kerschner, J.E., et al. Interleukin-1 receptor antagonist as an adjunct in the treatment of Haemophilus influenzae otitis media in the chinchilla. Laryngoscope 110, 1457-1461 (2000).

Kerschner, J.E., et al. MUC5AC expression in human middle ear epithelium of patients with otitis media. Arch Otolaryngol Head Neck Surg 136, 819-824 (2010).

Klein, J.O. The burden of otitis media. Vaccine 19 Suppl 1, S2-8 (2000).

Krasnici, S., et al., Effect of the surface charge of liposomes on their uptake by angiogenic tumor vessels. Int J Cancer, 2003. 105(4): p. 561-7.

Kurabi, A., et al. Peptides actively transported across the tympanic membrane: Functional and structural properties. PloS one 12, e0172158-0172117 (2017).

(56) References Cited

OTHER PUBLICATIONS

Kweon, S.M., et al. Synergistic activation of NF-kappaB by nontypeable H. influenzae and *S. pneumoniae* is mediated by CK2, IKKbeta-IkappaBalpha, and p38 MAPK. Biochem Biophys Res Commun 351, 368-375 (2006).
Leach, A.J., et al. Compared to placebo, long-term antibiotics resolve otitis media with effusion (OME) and prevent acute otitis media with perforation (AOMwiP) in a high-risk population: a randomized controlled trial. BMC Pediatr 8, 23 (2008).
Lighthall, J.G., et al. Control of Middle Ear Inflammatory and Ion Homeostasis Genes by Transtympanic Glucocorticoid and Mineralocorticoid Treatments. PloS one 10, e0119228 (2015).
Lim, J.H., et al. *Streptococcus pneumoniae* synergizes with nontypeable Haemophilus influenzae to induce inflammation via upregulating TLR2. BMC Immunol 9, 40 (2008).
Lin, J., et al. Mucin production and mucous cell metaplasia in otitis media. Int J Otolaryngol 2012, 745325 (2012).
Lo, C.T., et al. Poly(lactide-co-glycolide) nanoparticle assembly for highly efficient delivery of potent therapeutic agents from medical devices. Biomaterials 31, 3631-3642 (2010).
Makadia, H.K. et al. Poly Lactic-co-Glycolic Acid (PLGA) as Biodegradable Controlled Drug Delivery Carrier. Polymers (Basel) 3, 1377-1397 (2011).
Monroy, G.L., et al. Direct Analysis of Pathogenic Structures Affixed to the Tympanic Membrane during Chronic Otitis Media. Otolaryngol Head Neck Surg 159, 117-126 (2018).
Murphy, T.F. et al. Nontypable Haemophilus influenzae: a review of clinical aspects, surface antigens, and the human immune response to infection. Rev Infect Dis 9, 1-15 (1987).
O'Niel, M.B., et al. Tracking tympanostomy tube outcomes in pediatric patients with otitis media using an electronic database. Int J Pediatr Otorhinolaryngol 79, 1275-1278 (2015).
Ozyilmaz, E., et al. Major bacteria of community-acquired respiratory tract infections in Turkey. Jpn J Infect Dis 58, 50-52 (2005).
Paradise, J.L., et al. Otitis media in 2253 Pittsburgh-area infants: prevalence and risk factors during the first two years of life. Pediatrics 99, 318-333 (1997).
Pettigrew, M.M., et al. Microbial interactions during upper respiratory tract infections. Emerg Infect Dis 14, 1584-1591 (2008).
Al-mahallawi, et al., "Enhanced non invasive trans-tympanic delivery of ciprofloxacin through encapsulation into nano-spanlastic vesicles: Fabrication, in-vitro characterization, and comparative ex-vivo permeation studies." International Journal of Pharmaceutics 522 (2017) 157-164.
Abdelbary, et al., "Fabrication of levofloxacin polyethylene glycol decorated nanoliposomes for enhanced management of acute otitis media: Statistical optimization, trans-tympanic permeation and in vivo evaluation." International Journal of Pharmaceutics 559 (2019) 201-209.
Al-mahallawi, et al., "Nano-transfersomal ciprofloxacin loaded vesicles for non-invasive trans-tympanic ototopical delivery: In-vitro optimization, ex-vivo permeation studies, and in-vivo assessment." International Journal of Pharmaceutics 472 (2014) 304-314.
Sobhani, et al., "Nanoparticles of Chitosan Loaded Ciprofloxacin: Fabrication and Antimicrobial Activity." Adv Pharm Bull, 2017, 7(3), 427-432.
Takeuchi, et al., "Skin permeability and transdermal delivery route of 50-nm indomethacin-loaded PLGA nanoparticles." Colloids and Surfaces B: Biointerfaces 159 (2017) 312-317.
Kechai, et al., "Recent advances in local drug delivery to the inner eat." International Journal of Pharmaceutics 494 (2015) 83-101.
EP20798434.5—Extended European Search Report—Dec. 23, 2022.

* cited by examiner

TRANS-TYMPANIC MEMBRANE DELIVERY PLATFORM AND USES THEREOF

CROSS-REFERENCE TO RELATED APPLICATIONS

This application is a continuation of U.S. application Ser. No. 16/859,422 filed on Apr. 27, 2020, issuing as U.S. Pat. No. 11,197,820 on Dec. 14, 2021, which claims the benefit of priority to U.S. Provisional Application No. 62/840,632, filed Apr. 30, 2019, the disclosure of which are incorporated herein by reference in their entireties.

STATEMENT REGARDING FEDERALLY FUNDED RESEARCH OR DEVELOPMENT

Not applicable.

BACKGROUND

Otitis Media (OM) is the most common childhood infection and is a leading reason for pediatric office visits, new antibiotic prescriptions, and surgery in young children. The US healthcare system expends over $5B annually in treating this disease. OM is the most common cause of hearing loss in children and, therefore, also has the potential for additional serious developmental consequences. Bacterial infection, long term inflammation, and over production of mucins in the middle ear (ME) are hallmarks of the disease. OM is generally treated with systemic oral antimicrobial agents which, in part related to the frequency of treatment, have become far less effective as pathogens have developed resistance to these antimicrobial therapies. These systemic treatments also result in frequent adverse side effects including gastrointestinal (GI), cutaneous and, at times, life-threatening events. Systemic anti-inflammatory medication, while potentially effective in limiting some of the negative local inflammatory aspects of OM in the ME, such as mucin hyper-secretion and hearing loss, is not generally utilized because of the potential for negative off-target effects. Currently, many children with chronic OM undergo surgical intervention with tympanostomy tube placement (TTP), as there exist few alternative therapies. Accordingly, there remains a need in the art for noninvasive, targeted methods for delivering therapeutic agents to the middle ear while avoiding systemic exposure.

SUMMARY OF THE DISCLOSURE

This disclosure is related to methods and compositions for efficient delivery of cargo across the tympanic membrane. In particular, the methods and compositions of this disclosure provide cationic, anionic, and polymer-based nanoparticles for local, efficient, non-invasive delivery of therapeutic agents across the tympanic membrane.

In a first aspect, provided herein is a method of treating a subject having or suspected of having otitis media associated with a middle ear infection, the method comprising topically applying into the ear canal of an ear of the subject an aqueous suspension composition comprising nanoparticles and a pharmaceutically acceptable aqueous carrier, wherein the nanoparticles are cationic, anionic, or polymer-based, and comprise a therapeutically effective amount of one or more therapeutic agents; whereby, the topically applied nanoparticles diffuse through the ear's tympanic membrane, thereby delivering the one or more therapeutic agents to the middle ear and treating the otitis media. The otitis media can be acute otitis media. The otitis media can be chronic suppurative otitis media. The one or more therapeutic agents can be hydrophilic. The hydrophilic therapeutic agent can be an antimicrobial agent. The one or more therapeutic agents can be hydrophobic. The hydrophobic therapeutic agent can be an anti-inflammatory agent. The one or more therapeutic agents can comprise an anti-infection agent, and anti-inflammatory agent, and an anti-biofilm agent. The nanoparticles can have an average diameter size of about 100 nm. The nanoparticles can be cationic nanoparticles. Cationic nanoparticles can comprise cationic liposomes. The cationic liposomes can comprise cationic lipids selected from DOTAP, 3β-[N-(N',N'-dimethylaminoethane)-carbamoyl] cholesterol hydrochloride (DC-cholesterol-HCl), .1,2-Di-O-octadecenyl-3-trimethylammonium propane (chloride salt) (DOTMA), •

Dimethyldioctadecylammonium (Bromide Salt) (18:0 DDAB), CLinDMA, 6-lauroxyhexyl ornithinate (LHON), Dimethyldioctadecylammonium, 1,2-dioleyloxy-3-dimethylaminopropane (DODMA), Dimethyldioctadecylammonium bromide (DDMA), Dioctadecylamidoglycylspermidine (DOGS), N-(4-carboxybenzyl)-N,N-dimethyl-2,3-bis (oleoyloxy)propan-1-aminium (DOBAQ), 1,2-distearoyl-3-dimethylammonium-propane(18:0 DAP) and Dioctadecyldimethylammonium:monoolein. The nanoparticles can be anionic nanoparticles. Anionic nanoparticles can comprise anionic liposomes. The anionic liposomes can comprise anionic lipids selected from dihexadecylphosphate (DhP), phosphatidyl inositols, phosphatidyl serines (e.g., dimyristoyl phosphatidyl serine, dipalmitoyl phosphatidyl serine) phosphatidyl glycerols (e.g., dimyristoylphosphatidyl glycerol, dioleoylphosphatidyl glycerol, dilauryloylphosphatidyl glycerol, dipalmitoylphosphatidyl glycerol, di stearyloylphosphatidyl glycerol), phosphatidic acids (e.g., dimyristoyl phosphatic acid and dipalmitoyl phosphatic acid), and diphosphatidyl glycerol. The nanoparticles can be polymer-based nanoparticles. The polymer-based nanoparticles can comprise PLGA.

In another aspect, provided herein is a pharmaceutical composition for preventing and alleviating otitis media, the composition comprising a therapeutically effect amount of nanoparticles that comprise at least one therapeutic agent in aqueous suspension, wherein the nanoparticles have an average diameter size of about 50 nm to about 150 nm. The nanoparticles can have an average diameter size of about 100 nm.

In another aspect, provided herein is a method for trans-tympanic membrane delivery of a therapeutic agent, the method comprising topically applying into the ear canal of an ear of the subject an aqueous suspension composition comprising nanoparticles and a pharmaceutically acceptable aqueous carrier, wherein the nanoparticles comprise a therapeutically effective amount of a therapeutic agent, whereby, the topically applied nanoparticles diffuse through the ear's tympanic membrane, thereby delivering the therapeutic agent to the middle ear.

DETAILED DESCRIPTION

Figures 1A, 1B:
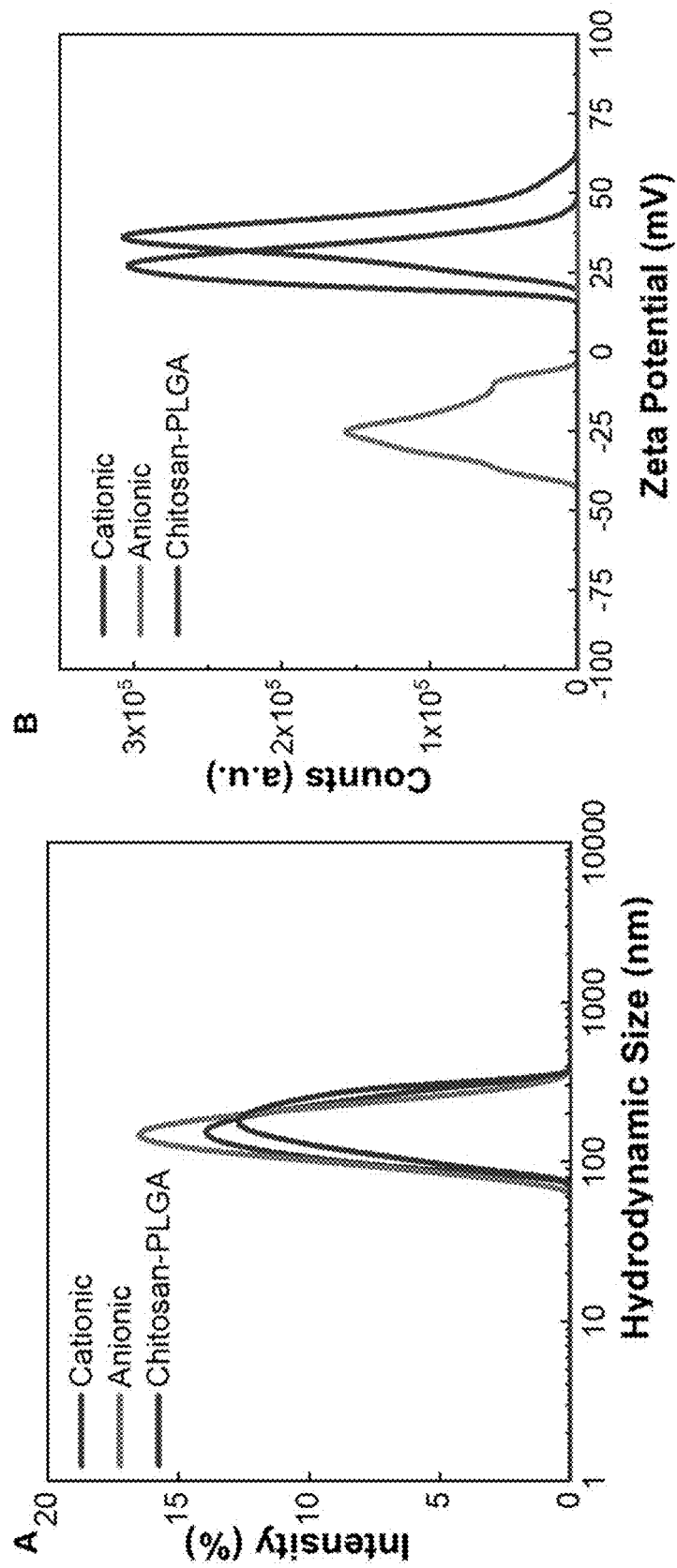
FIGS. 1A-1B demonstrate hydrodynamic size and zeta potential of charged nanoparticles. (A) The hydrodynamic size of both cationic, anionic, and Chitosan-PLGA antibiotic loaded nanoparticles was around 100 nm. (B) Zeta potential of anionic liposomes was −28 mV, cationic liposomes +37 mV and chitosan-PLGA nanoparticles is +31 mV.

All publications, including but not limited to patents and patent applications, cited in this specification are herein incorporated by reference as though set forth in their entirety in the present application.

The methods and compositions provided herein are based at least in part on the inventors' development of nanoparticle-based drug carriers for local non-invasive trans-tympanic membrane (TM) drug delivery for therapeutic agents such as antibiotics and steroid drugs. Also provided herein are uses of drug delivery platform for targeted, efficient treatment of inflammatory diseases of the middle ear such as acute otitis media (OM), chronic suppurative OM, otitis media with effusion, and chronic otitis media with effusion.

Advantages of the methods and compositions provided herein are multifold. For example, the impermeability of the tympanic membrane, resulting from tight junctions within the epithelial layer, has severely limited the efficacy of topically administered therapeutics to the ME cavity. Because of the TM's impermeability, conventional treatment methods for inflammatory conditions of the middle ear involve oral administration of antimicrobial agents and other therapeutic agents. Such systemic treatments frequently result in therapeutic resistance or adverse side effects. For chronic OM, particularly in children, treatment frequently involves surgical intervention with tympanostomy tube placement. To date, no alternative non-invasive therapies are known. In addition, most antibiotics pertinent to OM treatment are hydrophilic and have negligible penetration into the middle ear via direct application to the TM. The methods and compositions of this disclosure enable delivery across intact tympanic membranes following topical application of nanoparticle-based formulations of this disclosure, which is a far superior mode of delivery than oral delivery because of reduced likelihood of off-target effects and the ability to achieve therapeutic levels of drugs in middle ear.

Accordingly, in a first aspect, provided herein is a nanoparticle-based noninvasive trans-tympanic membrane delivery platform for treating conditions of the middle ear (ME). The delivery platform comprises nanoparticles comprising therapeutic cargo, where the cationic nanoparticles effectively and rapidly translocate into the middle ear cavity through the tympanic membrane, thereby delivering the therapeutic cargo to the middle ear. In some cases, the nanoparticles are cationic nanoparticles. In other cases, the nanoparticles are anionic. As used herein, the term "therapeutic cargo" refers to any molecule (including small molecules, macromolecules) or compound that provide a therapeutic or functional benefit to the targeted cell or tissue when delivered across the TM using the delivery platform of this disclosure. Therapeutic cargo include, without limitation, small molecular drugs (e.g., hydrophobic drugs, hydrophilic drugs), macromolecules (such as proteins, peptides, genes, antibodies, antigens, human growth factors, etc.), and nucleic acids.

As used herein, the term "cationic" refers to a molecule having a net positive surface charge. Cationic nanoparticles appropriate for the trans-TM delivery platform of this disclosure have a submicron size (about 1 nm to about 1000 nm) and positive net surface charge. Preferably, the cationic nanoparticles have an average size of about 50 nm to about 150 nm. In some cases, the cationic particles have an average size of about 100 nm.

As used herein, the term "anionic" refers to a molecule having a net negative surface charge. Anionic nanoparticles appropriate for the trans-TM delivery platform of this disclosure have a submicron size (about 1 nm to about 1000 nm) and positive net surface charge. Preferably, the anionic nanoparticles have an average size of about 50 nm to about 150 nm. In some cases, the anionic particles have an average size of about 100 nm.

In some cases, cationic or anionic nanoparticles comprise charged liposomes or polymeric nanoparticles. As used herein, the term "liposome" refers to a bilayer particle of amphipathic lipid molecules enclosing an aqueous interior space. Liposomes are typically produced as small unilamellar vesicles (SUVs), large unilamellar vesicles (LUVs) or multilamellar vesicles (MLVs). For example, cationic nanoparticles can be prepared using cationic liposome-forming lipids. A variety of cationic lipids have been reported for gene delivery applications, all or most of which can be adapted for trans-TM drug delivery. Exemplary cationic lipids suitable for use according to the methods and compositions provided herein include, without limitation, cationic DOTAP (1,2-dioleoyl-3-trimethylammonium-propane chloride salt), 3β-[N-(N',N'-dimethylaminoethane) carbamoyl] cholesterol (DC-cholesterol-HCl), dimethyldioctadecylammonium (DDA), CLinDMA (2-{4-[(3b)-cholest-5-en-3-yloxy] butoxy}-N,N-dimethyl-3-[(9Z, 12Z)-octadeca-9,12-dien-1-yloxy] propan-amine), 6-lauroxyhexyl ornithinate (LHON), Dimethyldioctadecylammonium (Bromide Salt, DDMA), Dioctadecyldimethylammonium: monoolein, 1,2-dioleyloxy-3-dimethylaminopropane (DODMA), Dioctadecylamidoglycylspermidine (DOGS), N-(4-carboxybenzyl)-N,N-dimethyl-2,3-bis (oleoyloxy) propan-1-aminium (DOBAQ), 1,2-distearoyl-3-dimethylammonium-propane (18:0 DAP), DOTMA (1,2-di-O-octadecenyl-3-trimethylammonium propane (chloride salt)), 18:0 DDAB (Dimethyldioctadecylammonium (Bromide Salt)).

Anionic nanoparticles can be prepared using anionic liposome-forming lipids. Exemplary anionic lipids suitable for use according to the methods and compositions provided herein include, without limitation, dihexadecylphosphate (DhP), phosphatidyl inositols, phosphatidyl serines (e.g., dimyristoyl phosphatidyl serine, dipalmitoyl phosphatidyl serine) phosphatidyl glycerols (e.g., dimyristoylphosphatidyl glycerol, dioleoylphosphatidyl glycerol, dilauryloylphosphatidyl glycerol, dipalmitoylphosphatidyl glycerol, di stearyloylphosphatidyl glycerol), phosphatidic acids (e.g., dimyristoyl phosphatic acid and dipalmitoyl phosphatic acid), and diphosphatidyl glycerol.

In some cases, nanoparticles of this disclosure are polymer-based nanoparticles. As used herein, the term "polymer-based nanoparticle" refers to submicron-sized (1 nm to 1000 nm) colloidal particles of polymer. Preferably, the nanoparticles have an average size of about 50 nm to about 150 nm. Therapeutic cargo can be adsorbed to or encapsulated by a cationic or anionic polymer-based nanoparticle. Preferably, the polymer-based nanoparticles comprise a biocompatible and biodegradable polymer such as poly(D,L-lactic-co-glycolic) acid (PLGA). For instance, the Examples describe successful TM delivery of nanoparticles comprising chitosan-PLGA. Other polymers useful for drug delivery as nanoparticles according to this disclosure include, without limitation, class poly(a-hydroxy acid)s, which include poly (glycolic acid) and the stereoisomeric forms of poly(lactic acid); copolymers of lactide and glycolide including poly (c-caprolactone) (PCL), and Poly(trimethylene carbonate) (P(TMC)); and synthetic biocompatible polymers such as lactide (PCLLA), poly-glutamic acid (PGlu), and poly(alkyl-cyanoacrylate), and poly(butyl-cyanoacrylate) (PBCA).

In some cases, nanoparticles of this disclosure are prepared using rare earth (lanthanide) oxide nanoparticles such as gadolinium oxide ($Gd_2O_3$) nanoparticles. In some cases, cationic nanoparticles are prepared by doping nanoparticles with lanthanide elements which form trivalent cations, Ln3+. Lanthanide elements include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

Preferably, nanoparticles comprising therapeutic cargo are prepared in aqueous suspension. In some cases, nanoparticles of this disclosure are prepared as a stable colloidal dispersion.

The delivery platform can be used to treat any disease or condition where a targeted delivery of therapeutic compounds across the tympanic membrane and into the middle ear can be useful, including, for example and without limitation, otitis media (OM), otitis media with effusion, and chronic otitis media with effusion, other conditions of the external, middle or inner ear, or other bodily organs or structures accessible from the ear canal. The particular therapeutic cargo of the nanoparticles will vary based on the disease or condition to be treated. Where the disease is acute or chronic OM caused by a bacterial or viral infection, the therapeutic cargo is preferably an anti-microbial agent such as an antibiotic and/or anti-viral agent. In some cases, the therapeutic cargo is an anti-inflammatory agent such as a steroidal compound (e.g., hydrocortisone, dexamethasone).

Exemplary antibiotics, anti-bacterials, and anti-infectives include sulfonamides (e.g., sulfanilamide, sulfadiazine, sulfamethoxazole, sulfisoxazole, para-aminobenzoic acid, or sulfacetamide), trimethoprim-sulfamethoxazole, quinolones (e.g., ciprofloxacin, ofloxacin, or nalidixic acid), beta-lactam antibiotics such as penicillins or cephalosporins, aminoglycosides (e.g., kanamycin, tobromycin, gentamycin C, amikacin, neomycin, netilmicin, streptomycin, or vancomycin), tetracyclines, chloramphenicol, and macrolides (e.g., erythromycin, clarithromycin, or azithromycin). Non-limiting examples of suitable penicillins include penicillin G, penicillin V, methicillin, oxacillin, nafcillin, ampicillin, and amoxicillin. Non-limiting examples of suitable cephalosporins include cephalothin, cefdinir, cefazolin, cephalexin, cefadroxal, cefamandole, cefoxitin, cefaclor, cefonicid, cefoletan, cefotaxime, ceftizoxime, ceftriaxone, cefditoren, and cefepime. Exemplary antibiotics useful for treating OM include penicillins such as amoxicillin and amoxicillin-clavulanate; sulfa-based combinations such as erythromycin-sulfisoxazole, trimethoprim-sulfamethoxazole; macrolides/azalides such as azithromycin or clarithromycin; second-generation cephalosporins such as cefaclor, cefprozil, cefuroxime axetil, or loracarbef; and third generation cephalosporins such as cefdinir, cefixime, cefpodoxime proxetil, ceftibuten, cefditoren, and ceftriaxone. Those skilled in the art can identify pharmacological agents and combine them as needed to achieve a desired effect. Therapeutic agents identified herein are simply a representative but non-exclusive list of possible agents.

In some cases, it will be advantageous for nanoparticles of this disclosure to comprise a second (or third, fourth, or more) therapeutic agent. For example, in some cases, cationic nanoparticles for TM delivery comprise multiple therapeutic agents such as, for example, a combination comprising an anti-infection agent, and anti-inflammatory agent, and an anti-biofilm agent. Such multifunctional NP formulations can be used for simultaneous delivery of multiple therapeutic agents for local OM treatment. As used herein, the term "anti-biofilm agent" refers to agents that exert anti-biofilm formation activity and/or prevent, reduce, or disrupt biofilm formation. Biofilm formation is the process in which microorganisms attach to a surface and form a multicellular association of bacteria and/or fungi. In some cases, anti-biofilm agents disrupt microbial quorum sensing (QS). The phrases "anti-biofilm formation activity" or "anti-quorum sensing activity", as these equivalent terms are used herein interchangeably, refer to the capacity of a substance to effect the prevention of formation of a biofilm of bacterial, fungal and/or other cells; and/or to effect a disruption and/or the eradication of an established and/or matured biofilm of bacterial, fungal and/or other cells; and/or to effect a reduction in the rate of buildup of a biofilm of bacterial, fungal and/or other cells on a surface of a substrate.

In other cases, nanoparticles of this disclosure comprise one or more antimicrobial agents (e.g., antibiotic, antiviral, antifungal) and further comprise an additional therapeutic agent as an anesthetic or analgesic for pain relief. Examples of anesthetics and analgesics include, without limitation, antipyrine, benzocaine, lidocaine, butamben, dibucaine, oxybuprocaine, pramoxine, proparacaine, proxymetacaine, tetracaine, chloroprocaine, cocaine, cyclomethycaine, dimethocaine, piperocaine, propoxycaine, novocaine, articaine, bupivacaine, etidocaine, levobupivacaine, mepivacaine, prilocaine, ropivacaine, methohexital, ketamine, prilocaine, thiopental, propofol, and trimecaine; essential oils, such as clove oil or fennel oil, or active components of such essential oils, such as menthol, eugenol, linalool, or fenchone; or mixtures of these anesthetics and analgesics.

In some cases, a NP solution or formulation of this disclosure is provided as a unit dosage form in a hermetically sealed container such as an ampoule or vial indicating the quantity of active agent. Where the composition is to be administered by instillation into the ear canal, it can be dispensed with a sprayer, dropper, syringe, infusion bottle, or other suitable applicator. Alternatively, the hermetically sealed container can be a prefilled syringe or dropper, in which a seal is broken to permit use of the syringe for application of the NP solution to the ear canal. Conventional applicators, such as sprayers, syringes, and droppers, can be selected to provide suitable amounts and placement of the formulation within the ear canal. The choice of a suitable applicator and method of application is routine for the ordinarily-skilled artisan. The formulations can be stored in a single-dose or multi-dose container prior to application. A formulation can be provided as small volume of material that is well dispersed (e.g., in a thin layer) on the tympanic membrane.

In some cases, a NP solution or formulation of this disclosure is provided as a pharmaceutical composition, which means a composition comprising therapeutically effective amounts of cationic nanoparticles of this disclosure together with a pharmaceutically-acceptable carrier. As used herein, the term "pharmaceutically acceptable carriers" refers to diluents, preservatives, solubilizers, emulsifiers, adjuvants, aqueous and non-aqueous solutions, suspensions, and emulsions. Aqueous carriers include, without limitation, water, alcoholic/aqueous solutions, emulsions or suspensions, including saline, phosphate buffered saline (PBS), Hepes buffered saline (HPS), and other buffered solutions. Examples of non-aqueous solvents are propylene glycol, polyethylene glycol, vegetable oils such as olive oil, and organic esters such as ethyl oleate. Pharmaceutically acceptable carriers suitable for the pharmaceutical compositions of this disclosure are well known to those skilled in the art.

Methods

In another aspect, provided herein are methods for treating a condition of the middle ear or inner ear, e.g., otitis media. In certain embodiments, the method comprises administering the delivery platform to an ear canal of a subject in need of such treatment. In particular, the delivery platform of this disclosure can be used to deliver a therapeutically effective amount of a therapeutic cargo to a subject in need thereof.

As used herein, the term "subject" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex. Preferably, "subject in need thereof" refers to an animal or human subject who has been diagnosed with, is suspected of having, or is at risk of having a disease or condition requiring treatment with formulations provided herein.

As used herein, a "therapeutically effective amount" refers to an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. The optimum effective amounts can be readily determined by one of ordinary skill in the art using routine experimentation.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. For purposes of this disclosure, "treating" or "treatment" describes the management and care of a patient for the purpose of combating the disease, condition, or disorder. The terms embrace both preventative, i.e., prophylactic, and palliative treatment. "Treating" includes the administration of a compound of present invention to prevent the onset of the symptoms or complications, alleviating the symptoms or complications, or eliminating the disease, condition, or disorder.

Generally, the method comprises delivering cationic, anionic, or polymer-based nanoparticles of this disclosure into the ear canal, e.g., into the middle ear, by any of a variety of methods, some of which are known in the art. For example, a composition can be administered via any medically acceptable means for application of a pharmaceutical composition to the ear canal, e.g., by topical administration to the external auditory canal (EAC), by insertion of a needleless syringe or dropper into the auditory canal. It will be appreciated that care should be used to avoid piercing or puncturing the tympanic membrane. Prophylactic treatment against recurrence of, for example, a middle ear infection may be provided in the same manner, utilizing nanoparticles comprising a prophylactically effective antibiotic or other medicament.

Advantageously, the methods provided herein provide rapid, localized delivery of the therapeutic cargo to the middle ear. For example, delivery of therapeutic cargo through the TM and into the middle ear can occur within about 15 minutes (e.g., within about 1, 2, 3, 4, 5, 6, 7, 8, 9, 10, 11, 12, 13, 14, 15 minutes) of applying an aqueous suspension of nanoparticles described herein to the EAC. In view of such rapid, localized efficacy, the delivery platform provided herein is a significant improvement over the conventional oral regimen for treating OM. Targeted delivery through the TM eliminates systemic off-target effects and does not negatively affect the mechanical properties of TM for extended durations.

Administration is repeated as required to achieve the therapeutically effective dosage level for the particular therapeutic cargo. Those of ordinary skill in the art will be familiar with, and readily able to select, dosing regimens suitable for following to treat a particular ear disease or condition. The dosing regimen selected will be in accord with established clinical protocols for delivery and use of the particular formulations described herein.

Articles of Manufacture

In another aspect, the present invention provides articles of manufacture useful for treating acute or chronic otitis media in pediatric and adult populations according to the methods provided herein. In certain embodiments, the article of manufacture is a kit comprising nanoparticles comprising therapeutic cargo. Preferably, the therapeutic cargo comprises one or more antimicrobial agents such as an antibiotic and/or anti-viral agent. In some cases, the cationic nanoparticles are provided in the kit as is formulation for delivery as drops into the ear canal and to the tympanic membrane. Preferably, the formulation is provided in one or more unit dosage forms. In some cases, the kit also comprises instructions for performing the treatment methods provided herein.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." The term "consisting essentially of" means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention.

EXAMPLE

Otitis media (OM) is typically treated with systemic oral antimicrobial agents. These systemic treatments frequently result in therapeutic resistance or cause adverse side effects. Currently, many children with chronic OM undergo surgical intervention with tympanostomy tube placement and no alternative non-invasive therapies exist. The impermeability of tympanic membrane (TM), driven by tight junctions on the epithelial layer has strongly limited the topical delivery efficacy of therapeutics to the middle ear (ME) cavity. Increasing the therapeutic flux through TM is critical for success of topical treatment. This section demonstrates the utility of multiple cationic and anionic charged nanoparticle-based drug carriers for local non-invasive trans-TM drug delivery for antibiotics.

It was hypothesized that charged nanoparticles (NPs) applied topically to the external auditory canal (EAC) can effectively and rapidly translocate therapeutics into the ME cavity through the TM via enhanced diffusion. To test this hypothesis, three antibiotic loaded cationic and anionic NP formulations for acute and chronic OM were synthesized and characterized. Specifically, delivery efficacy enhancements of these formulations were tested through the TM using an ex vivo chinchilla model.

Methods:

To investigate the role of NP charge enhancing Fick's diffusion across TM, cationic DOTAP (1,2-dioleoyl-3-trimethylammonium-propane) (~100 nm, charge +37 mV) and anionic DOPG (1,2-dioleoyl-sn-glycero-3-phospho-(1'-rac-glycerol) based liposomes (~100 nm, charge −30 mV) were synthesized (FIGS. 1A-1B). The charged liposomes were prepared by standard thin film hydration method with 20 mg of total lipids. The cationic DOTAP liposomes were prepared by using DOTAP:DOPC (1,2-Dioleoyl-sn-glycero-3-phosphocholine) (40:60 molar ratio) in 2 ml of chloroform [1]. The resulted lipid film after rotatory evaporation was hydrated by use of 2 ml of Ciprofloxacin HCL dissolved in PBS buffer (1×, pH=4), followed by vortexing and extruding, resulting in a homogeneous suspension of liposomes. The anionic liposomes were prepared by using DOPG:DOPC:DOPE (1,2-dioleoyl-sn-glycero-3-phosphoethanolamine) (16:80:4) in 2 ml of chloroform [2]. The thin lipid film obtained after rotatory evaporation is dissolved was hydrated by use of 2 ml of CFX (Ceftriaxone) dissolved in HBS (Hepes buffered saline) buffer (1×, pH=7.2), followed by vortexing and extruding, resulting in a homogeneous suspension of liposomes. This homogenous suspension was centrifuged and liposomes were suspended in 2 mL of HBS buffer (pH=7.2). The hydrodynamic size and zeta potential of liposomes were determined by running samples on a Malvern Zetasizer 3600 (Malvern Instruments).

Further, to verify the effect of cationic charge in enhancing the delivery of drug across TM with a sustained drug release formulation, polymer-based Chitosan-PLGA (poly (lactic-co-glycolic acid) nanoparticles (~100 nm, charge +30 mV) loaded with CFX were synthesized (FIGS. 1A-1B). Antibiotic-loaded Polymer nanoparticles were generally prepared using a double-emulsion solvent evaporation method [3]. For these preparations, a solution of CFX in 1× HBS buffer (pH 7.2) in the ratios of 1:2, (w/w) antibiotic to polymer was emulsified in a PLGA solution in dichloromethane (DCM, 2 mL) using a sonicator. This primary water-in-oil (W/O) phase was subsequently added drop-wise to 1% PVA (Poly Vinyl Alcohol) solution (second aqueous phase). A second sonication was performed to form the water-in-oil-in-water (W1/O/W2) emulsion with 0.5% PVA and 80 mg of chitosan. Finally, the nano-emulsion was stirred overnight at room temperature to evaporate DCM. The resulting nanoparticles suspension was centrifuged with addition of water and washed to remove trace amounts of DCM and free antibiotics.

The efficacy of these NPs to deliver drug was tested by ex vivo experiments. 200 μl NPs aqueous suspension was applied to the external auditory canal (EAC) of excised chinchilla auditory bullae maintained with PBS buffer in middle ear and was sampled at varying time-intervals to detect diffusion of NPs and their ability to deliver drugs. The drug delivering capacity of these biocompatible drug delivery systems was determined by quantifying the collected samples by HPLC assays.

Figures 2A, 2B, 2C:
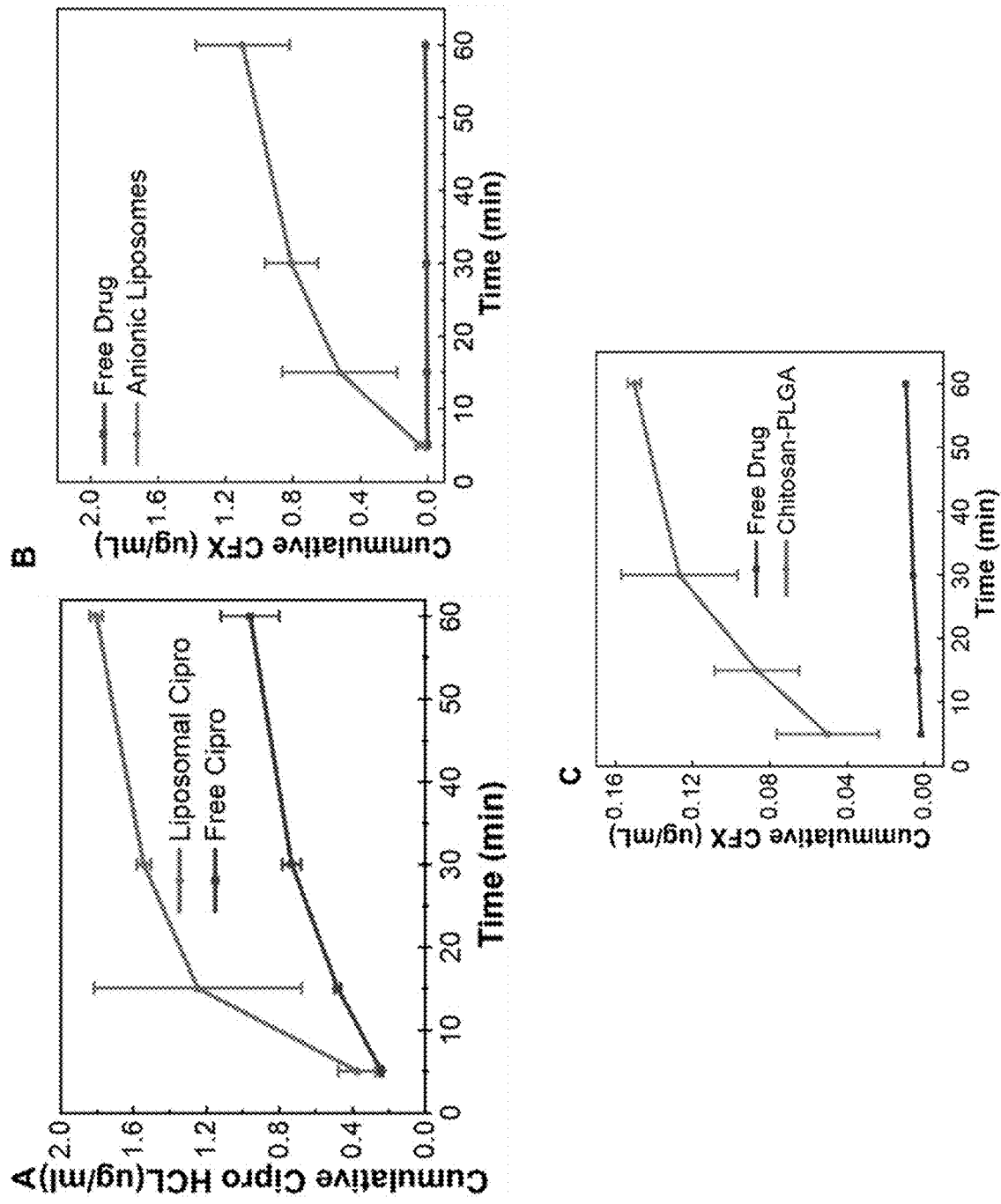
FIGS. 2A-2C demonstrate ex vivo transfer of Ciprofloxacin (Cipro HCL) and Ceftriaxone (CFX) across the tympanic membrane. Data are the means (n=3) for all the conditions. (A) Cationic liposomes were loaded with Cipro HCL (1 mg). (B) Anionic liposomes (1.5 mg) and (C) Chitosan-PLGA nanoparticles were loaded with CFX (35 μg). Each of these nanoparticles were compared with equivalent amount of free drug.

Results:

For both the antibiotic cargoes, significantly enhanced transport of drugs to the middle ear was detected within about 5 to about 60 minutes of application compared to minimal or undetected levels in the middle ear for equivalent free drug application. The cationic liposomes with Ciprofloxacin HCL delivered 1.6 µg/ml in 60 min (FIG. 2A). The anionic liposomes with Ceftriaxone (CFX) delivered ~1.1 µg/ml. In both the cases, it seems the dose of antibiotic delivered is almost equivalent to the MIC (~1 µg/ml) for SP and NTHi strains (FIG. 2B). The CFX loaded Chitosan-PLGA nanoparticles loaded with Ceftriaxone delivered 0.16 µg/ml in 60 min (FIG. 2C). The dose delivered by PLGA based nanoparticles was lower than liposomal particles but compared to free drug delivery the delivered drug dose was 6-10 fold higher.

Conclusion: In summary, these results demonstrate that local, non-invasive trans-TM delivery of antibiotics and steroids is possible using cationic NPs formulations. Consequently, non-invasive delivery of therapeutic levels of drugs such as antimicrobials is feasible with a topical ear-drop type application.

REFERENCES

1. Strieth, S., et al., *Neovascular targeting chemotherapy: encapsulation of paclitaxel in cationic liposomes impairs functional tumor microvasculature*. Int J Cancer, 2004. 110(1): p. 117-24.
2. Krasnici, S., et al., *Effect of the surface charge of liposomes on their uptake by angiogenic tumor vessels*. Int J Cancer, 2003. 105(4): p. 561-7.
3. Al-Nemrawi, N. K., et al., *Low Molecular Weight Chitosan-Coated PLGA Nanoparticles for Pulmonary Delivery of Tobramycin for Cystic Fibrosis*. Pharmaceuticals (Basel), 2018. 11(1).

We claim:

1. A pharmaceutical composition for preventing and alleviating otitis media, the composition comprising an aqueous suspension composition comprising cationic liposomes comprising a therapeutically effective amount of one or more therapeutic agents and a pharmaceutically acceptable aqueous carrier, wherein the cationic liposomes comprise 1,2-dioleoyl-3-trimethylammonium-propane (DOTAP), 3β-[N-(N',N'-dimethylaminoethane)carbamoyl] cholesterol (DC-cholesterol), and 1,2-dioleoyl-sn-glycero-3-phosphocholine (DOPC) and have an average diameter size of about 50 nm to about 150 nm and a zeta potential from +25 mV to +50 mV, wherein, when topically applied to the tympanic membrane of the ear, the cationic liposomes diffuse through the ear's tympanic membrane, thereby delivering the one or more therapeutic agents to the middle or inner ear and treating the otitis media.

2. The pharmaceutical composition of claim 1, wherein the cationic liposomes further comprise an additional cationic lipid selected from dimethyldioctadecylammonium (DDA), CLinDMA (2-{4-[(3b)-cholest-5-en-3-yloxy]butoxy}-N,N-dimethyl-3-[(9Z,12Z)-octadeca-9,12-dien-1-yloxy] propan-amine), 6-lauroxyhexyl orithinate (LHON), Dimethyldioctadecylammonium (DDMA), Dioctadecyldimethylammonium: monoolein, 1,2-dioleyloxy-3-dimethylaminopropane (DODMA), Dioctadecylamidoglycylspermidine (DOGS), N-(4-carboxy benzyl)-N,N-dimethy 1-2,3-bis(oleoyloxy) propan-1-aminium (DOBAQ), 1,2-distearoyl-3-dimethylammonium-propane (18:0 DAP), DOTMA (1,2-di-O-octadecenyl-3-trimethylammonium propane), 18:0 DDAB (Dimethyldioctadecylammonium), and combinations thereof.

3. The pharmaceutical composition of claim 1, wherein the cationic liposomes further comprise 1,2-dioleoyl-sn-glycero-3-phosphoethanolamine (DOPE).

4. The pharmaceutical composition of claim 2, wherein the further cationic lipid is selected from DOTMA, 18:0 DDAB, CLinDMA, LHON, Dimethyldioctadecylammonium, Dioctadecyldimethylammonium: monoolein, and combinations thereof.

5. The pharmaceutical composition of claim 1, wherein the one or more therapeutic agent is an antimicrobial agent.

6. The pharmaceutical composition of claim 1, wherein the one or more therapeutic agents is hydrophobic.

7. The pharmaceutical composition of claim 6, wherein the hydrophobic therapeutic agent is an anti-inflammatory agent.

8. The pharmaceutical composition of claim 1, wherein the one or more therapeutic agents comprises an anti-infection agent, and anti-inflammatory agent, and an anti-biofilm agent.

* * * * *

UNITED STATES PATENT AND TRADEMARK OFFICE
CERTIFICATE OF CORRECTION

PATENT NO. : 12,285,519 B2
APPLICATION NO. : 17/548173
DATED : April 29, 2025
INVENTOR(S) : Amit Joshi et al.

It is certified that error appears in the above-identified patent and that said Letters Patent is hereby corrected as shown below:

In the Claims

Claim 2, Column 12, Line 15, "orithinate" should be --ornithinate--.

Signed and Sealed this
Seventeenth Day of June, 2025

Coke Morgan Stewart
*Acting Director of the United States Patent and Trademark Office*